(12) United States Patent
Felder et al.

(10) Patent No.: US 9,332,758 B2
(45) Date of Patent: May 10, 2016

(54) COMPOSITIONS CONTAINING 1,2-BENZISOTHIAZOLIN-3-ONE

(75) Inventors: Patrick T. Felder, Grabs (CH); Anton O. Mettler, Buchs (CH); Pierre M. Lenoir, Richterswil (CH)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 275 days.

(21) Appl. No.: 13/187,599

(22) Filed: Jul. 21, 2011

(65) Prior Publication Data

US 2012/0035229 A1 Feb. 9, 2012

Related U.S. Application Data

(60) Provisional application No. 61/371,811, filed on Aug. 9, 2010.

(51) Int. Cl.
*A01N 43/80* (2006.01)
*A01P 15/00* (2006.01)

(52) U.S. Cl.
CPC ...................... *A01N 43/80* (2013.01)

(58) Field of Classification Search
CPC ........ A01N 43/80; A01N 25/04; A01N 35/08
See application file for complete search history.

(56) References Cited

U.S. PATENT DOCUMENTS

| | | | |
|---|---|---|---|
| 5,160,666 A | 11/1992 | Lindner et al. | |
| 5,919,348 A | 7/1999 | Friedrich et al. | |
| 6,306,413 B1 | 10/2001 | Payne | |
| 6,361,788 B1 * | 3/2002 | Antoni-Zimmermann et al. | 424/406 |
| 7,652,048 B2 | 1/2010 | Bussmann | |
| 2004/0247626 A1 | 12/2004 | Berg et al. | |
| 2006/0140987 A1 | 6/2006 | Reeve | |
| 2007/0275945 A1 | 11/2007 | Lindner | |
| 2008/0318774 A1 | 12/2008 | Patel et al. | |
| 2010/0075939 A1 | 3/2010 | Lindner | |
| 2010/0152287 A1 | 6/2010 | Uhr | |

FOREIGN PATENT DOCUMENTS

| | | | |
|---|---|---|---|
| BR | 2007005356 | 8/2008 | |
| CN | 101570519 | 11/2009 | |
| CN | 101695297 | 4/2010 | |
| DE | RD460065 | 8/2002 | |
| DE | RD 460065 | * 8/2010 | |
| EP | 1 987 716 | * 11/2008 | ............. A01N 25/04 |
| EP | 1987716 | 11/2008 | |
| JP | 04208204 | 7/1992 | |
| JP | 2005213172 | 8/2005 | |
| WO | 2008136917 | 11/2008 | |
| WO | 2008155026 | 12/2008 | |
| WO | 2009103724 | 8/2009 | |

OTHER PUBLICATIONS

"Rhodopol® 50 MD" at /www.matweb.com/search/ data sheet text. aspx?matguid=583de3165c0442519801c9186d34bdbb (retrieved from the internet May 30, 2013).*

* cited by examiner

*Primary Examiner* — Dennis Heyer
(74) *Attorney, Agent, or Firm* — Tifani M. Edwards

(57) ABSTRACT

In a first aspect of the present invention, there is provided a composition comprising 1,2-benzisothiazolin-3-one dispersed in an aqueous medium and further comprising one or more polysaccharide; wherein either
(a) said composition comprises no surface-active compound, or
(b) said composition comprises one or more surface-active compounds, and the amount of said surface-active compounds in said composition is less than 0.4% by weight based on the weight of said composition.

3 Claims, No Drawings

COMPOSITIONS CONTAINING 1,2-BENZISOTHIAZOLIN-3-ONE

BACKGROUND 1,2-Benzisothiazolin-3-one (BIT) is an effective biocide that is employed, for example, for killing microorganisms (including, for example, bacteria, fungi, molds, yeasts, etc.) in useful aqueous compositions such as, for example, latices. BIT has low solubility in water when the pH is 7.5 or lower, and so it is common to provide BIT in the form (called an "aqueous BIT dispersion") of BIT particles dispersed in water. It is often desired to provide BIT in a form (called a "BIT concentrate") that has higher concentration of BIT than is needed for control of microorganisms in useful aqueous compositions. An appropriate amount of the BIT concentrate could be added to a useful aqueous composition to achieve the concentration of BIT that is needed for control of microorganisms in the useful aqueous composition. To be useful, a BIT dispersion concentrate (i.e., a BIT dispersion that is also a BIT concentrate) should have a useful viscosity, and it should be stable.

U.S. Pat. No. 6,306,413 describes compositions that contain BIT, dispersant, and Xanthan gum. Many dispersants are not approved by government bodies for use in compositions that come into indirect contact with food.

It is desired that a BIT dispersion concentrate contains as many ingredients as possible that are approved for use in compositions that come into indirect contact with food. One way to achieve this goal is to eliminate ingredients that are not approved for indirect contact with food. Therefore it is desired to provide a BIT dispersion concentrate that is stable, that has viscosity within a useful range, and that has little or no dispersant.

STATEMENT OF THE INVENTION

In one aspect of the present invention, there is provided a composition comprising 1,2-benzisothiazolin-3-one dispersed in an aqueous medium and further comprising one or more polysaccharide; wherein either (a) said composition comprises no surface-active compound, or (b) said composition comprises one or more surface-active compound, and the amount of said surface-active compound in said composition is less than 0.4% by weight based on the weight of said composition.

DETAILED DESCRIPTION

As used herein, a substance is "dissolved" in a liquid solvent if individual molecules of the substance are distributed throughout the solvent to form a solution. In a solution, the solute does not agglomerate or phase separate from the solvent during storage for long periods of time (e.g., for 7 days or more at 25° C.).

As used herein, particles are "dispersed" in a liquid medium if individual particles are distributed through throughout the liquid medium. Particles in a dispersion have median particle size of 100 nm or larger. Dispersed particles may be solid, liquid (if not miscible with the liquid medium) or gas.

An aqueous medium is a composition that is liquid at 25° C. and that contains 50% or more water by weight based on the weight of the aqueous medium. Substances that are dissolved in the aqueous medium are considered herein to be part of the aqueous medium, and substances dispersed in the aqueous medium are not considered herein to be part of the aqueous medium.

As used herein, a compound is "water insoluble" if the maximum amount of that compound that can be dissolved in water at 25° C. is 1 gram or less of the compound in 99 grams of water. As used herein, a compound is "water soluble" if more 1 gram of the compound can be dissolved in 99 grams of water at 25° C.

A "polymer," as used herein and as defined by F W Billmeyer, JR. in Textbook of Polymer Science, second edition, 1971, is a relatively large molecule made up of the reaction products of smaller chemical repeat units. A polymer is made of more than 10 repeat units and has molecular weight of more than 1,000. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

As used herein, a "surface-active" compound is a compound that is a dispersant, a surfactant, or both.

As used herein, an "organic solvent" is an organic compound that is liquid at 25° C.

The present invention involves the use of 1,2-benzisothiazolin-3-one (BIT). BIT is provided in the form of a collection of particles that are solid at 25° C. The particles in such a collection, including individual particles, aggregates, and agglomerates, range in size from 1 micrometer to 500 micrometer. Such a collection normally contains approximately 85% BIT and approximately 15% water, by weight. Such a collection appears to be a powder, though it is often called a "paste."

In the composition of the present invention, the particles of BIT are dispersed in an aqueous medium. Preferred aqueous media have water content, by weight based on the weight of the aqueous medium, of 75% or more. The preferred amount of BIT in the composition of the present invention, by weight based on the weight of the composition of the present invention, is 5% or more; more preferred is 10% or more. Independently, the preferred amount of BIT in the composition of the present invention, by weight based on the weight of the composition of the present invention, is 40% or less; more preferred is 30% or less; even more preferred is 25% or less.

The composition of the present invention contains one or more polysaccharide. A polysaccharide is a polymer made of more than 10 repeat units, where the repeat units are monosaccharides. Preferred are polysaccharides having 50 or more repeat units; more preferred are 75 or more repeat units. Preferred polysaccharides are water soluble. Preferred polysaccharides are cellulose ethers, derivatives of cellulose ether, gums, and mixtures thereof.

Cellulose ethers and their derivatives are made by alkylation of cellulose and, optionally, additional chemical modification. Preferred cellulose ethers and their derivatives are water soluble. Among cellulose ethers and their derivatives, preferred are hydroxyethylcellulose, sodium carboxymethylcellulose, and hydroxypropylmethylcellulose; more preferred is hydroxyethylcellulose.

Gums are polysaccharides produced by biological systems. Preferred gums are water soluble. Preferred gums have weight-average molecular weight of 500,000 or more; more preferred is 1 million or more. Among the gums, preferred is xanthan gum.

More preferred polysaccharides are hydroxyethylcellulose, xanthan gum, and mixtures thereof.

In the composition of the present invention, the preferred amount of polysaccharide, by weight based on the weight of the composition, is 0.5% or more; more preferably 0.6% or more. Independently, in the composition of the present invention, the preferred amount of polysaccharide, by weight based on the weight of the composition, is 1.5% or less; more preferably 1% or less; more preferably 0.8% or less. In some embodiments, the only polysaccharide is one or more polysaccharide selected from cellulose ethers, derivatives of cellulose ethers, and mixtures thereof, and in such embodiments, the preferred amount of polysaccharide is 0.7% by weight or higher, based on the weight of the composition.

The composition of the present invention contains little or no surface-active compound. That is, the composition of the present invention contains little or no dispersant, and it contains little or no surfactant.

Dispersants are polymers that adsorb onto the surfaces of particles of inorganic compounds that are insoluble in water, when those particles are mixed with water. At least one portion of a dispersant molecule (the "anchoring" group) has compatibility with one or more inorganic compounds that are insoluble with water. At least one other portion of the dispersant molecule provides compatibility with water. Dispersants are usually much weaker than surfactants at reducing the surface tension of water.

Dispersants include anionic dispersants, nonionic dispersants, and mixtures thereof. Anionic dispersants include, for example, homopolymers and random copolymers that contain carboxyl monomer units such as polymerized units of acrylic acid, methacrylic acid, or maleic anhydride. Anionic dispersants also include, for example, hydrophilic polymers attached to an "anchoring group." Hydrophilic polymers include, for example, polyacrylic acid and polymethacrylic acid. Anchoring groups include, for example, amino(bismethylenephosphonic acid) groups, alkyl phenol groups, and amine-containing polymer blocks (such as, for example, polyvinyl pyridine and polydimethylaminoethyl methacrylate). Anionic dispersants include, for example, sodium lignin sulphonate and the sodium salts of condensates of naphthalene sulphonic acid and formaldehyde.

Nonionic dispersants include, for example, dispersants that are block copolymers of ethylene oxide and propylene oxide.

A surfactant is a compound whose molecule has a hydrophobic portion and a hydrophilic portion. The category of surfactants includes compounds commonly labeled as "surfactants" and also includes emulsifiers and wetting agents. Surfactants may be cationic, anionic, zwitterionic, or nonionic. The hydrophilic portion of the molecule of an anionic surfactant is anionic. Nonionic surfactants are usually polymeric; polymeric nonionic surfactant molecules are often block copolymers, with a hydrophilic block (such as, for example, poly(ethylene oxide)) and a hydrophobic block (such as, for example, poly(propylene oxide)). Surfactants are usually more effective than dispersants at reducing the surface tension of a water solution.

The sum of the amounts of all surface-active compounds in the composition of the present invention may be zero or may be larger than zero. The sum of the amounts of all surface-active compounds in the composition of the present invention is also less than 0.4% by weight based on the weight of the composition. Preferred are compositions in which the sum of the amounts of all surface-active compounds, by weight based on the weight of the composition, is 0.4% or less; more preferred is 0.2% or less; more preferred is 0.1% or less; most preferred is zero.

Some embodiments of the composition of present invention contain clay. When clay is used, preferred is smectite clay. When clay is used, the preferred amount is, by weight based on the weight of the composition of the present invention, 1.5% or less; more preferred is 1% or less; more preferred is 0.5% or less. Preferred embodiments contain no clay.

Some embodiments of the composition of the present invention contain one or more acid, one or more base, one or more salt, or a combination thereof. Acids, bases, and/or salts may be added to adjust the pH value of the composition and/or to provide buffering to maintain the pH at a desired value. Preferred compositions have pH of 1.5 to 7.5. More preferred are compositions with pH of 2.0 or higher; more preferred is 2.5 or higher.

Preferred compositions of the present invention contain little or no acrylic polymer. Acrylic polymers contain 50% or more by weight, based on the weight of the polymer, polymerized units of acrylic monomers. Acrylic monomers are acrylic acid, methacrylic acid, substituted or unsubstituted amides thereof, and substituted or unsubstituted esters thereof. Preferred are compositions in which the amount of acrylic polymer, by weight based on the weight of the composition, is less than 0.4%; more preferred is 0.2% or less; more preferred is 0.1% or less; most preferred is zero.

Preferred compositions of the present invention contain little or no polymeric thickener that is not a polysaccharide. Polymeric thickeners are polymers that, when added to water in relatively small amounts raise the viscosity of the water. That is, when 1 gram or thickener is added to 99 grams of water (and, if necessary, the pH of the water is adjusted), the viscosity of the water is raised by a factor of 2 or higher. Some polymeric thickeners, for example, are polymers that are soluble in water. Some polymeric thickeners, for example, are latex polymers that are not soluble in water and that swell in water when the pH is raised above a critical value. Preferred are compositions in which the amount of polymeric thickener that is not a polysaccharide, by weight based on the weight of the composition, is less than 0.4%; more preferred is 0.2% or less; more preferred is 0.1% or less; most preferred is zero.

In preferred compositions of the present invention, the total amount of all surface-active compounds and all polymeric thickeners that are not polysaccharides in said composition is equal to or greater than zero and is less than 0.4% by weight based on the weight of the composition. The total amount of all surface-active compounds and all polymeric thickeners that are not polysaccharides in said composition that is more preferred is, by weight based on the weight of the composition, less than or equal to 0.2%; more preferred is less than or equal to 0.1%; most preferred is zero.

Preferred compositions of the present invention contain little or no polymer of any kind that is not a polysaccharide. Preferred are compositions in which the amount of polymer that is not a polysaccharide, by weight based on the weight of the composition, is less than 0.4%; more preferred is 0.2% or less; more preferred is 0.1% or less; most preferred is zero.

Some compositions of the present invention contain, in addition to BIT, one or more additional biocides. Biocides are compounds that kill microbial life. Additional biocides may be chosen, for example, from formaldehyde-releasing biocides, aldehydes, urea-based biocides, quaternary ammonium biocides, phenolic biocides, halogen-containing biocides, organometallic biocides, organosulfur biocides, heterocyclic biocides, biguanide biocides, other nitrogen-containing biocides, alcohol biocides, and mixtures thereof. When one or more additional biocide is present, preferred additional biocides are biocides that are water soluble. Some suitable water-soluble biocides are, for example, water-soluble derivatives of 3-isothiazolone. Suitable water-soluble biocides include, for example, 5-chloro-2-methyl-4-isothiazolin-3-one (CMI), 2-methyl-4-isothiazolin-3-one (MI), bronopol, Dimethylol Dimethyl Hydantoin (DMDMH), ethylenedioxydimethanol (EDDM), glutaraldehyde, glyoxal, Tetrahydro-1,3,4,6-tetrakis(hydroxymethyl)imidazo[4,5-d] imidazole-2,5(1H,3H)-dione (CAS Registry number 5395-50-6, also called tetramethylolacetylene diurea or TMDU), and mixtures thereof.

When one or more water-soluble biocide is used, any amount of water-soluble biocide above zero is contemplated. When one or more water-soluble biocide is used, the preferred amount of water-soluble biocide is, by weight based on the weight of the composition, 0.3% or more; more preferred is 1% or more; more preferred is 2% or more; more preferred is 5% or more. Independently, when one or more water-soluble biocide is used, the preferred amount of water-soluble biocide is, by weight based on the weight of the composition, 25% or less; more preferred is 15% or less; more preferred is 12% or less; more preferred is 10% or less. When CMI or a mixture of CMI and MI is included, the preferred amount of CMI or of the mixture of CMI and MI is 0.3% to 2% by weight based on the weight of the composition.

In some of the embodiments in which one or more water-soluble biocide is used, one or more of the water-soluble biocides may be sensitive to the pH of the solution. That is, at pH above 5, such biocides become increasingly unstable as the pH is raised. In such embodiments, the pH is preferably 7.5 or lower; more preferably 6.0 or lower; more preferably 5.0 or lower.

In some embodiments, the composition contains, in addition to BIT, one or more biocide that is not soluble in water. Among such embodiments, the preferred amount of biocide that is not BIT and that is not soluble in water is 5% or less by weight based on the weight of the composition.

Preferred compositions of the present invention contain little or no biocide other than BIT that is not soluble in water. Preferred are compositions in which the amount of biocide other than BIT that is not soluble in water is, by weight based on the weight of the composition, 1% or less; more preferred is 0.3% or less; more preferred is 0.1% or less; most preferred is zero.

Whether any biocide is or is not present in addition to BIT, the preferred amount of total biocide (i.e., the sum of the amounts of all biocides) in the composition of the present invention is, by weight based on the weight of the composition, 15% to 50%; more preferred is 15% to 35%; more preferred is 15% to 25%.

The composition of the present invention is normally made by a process that includes placing BIT paste (as described herein above), water, polysaccharide, and, optionally, other ingredients into a ball mill and milling the mixture. The result is a dispersion of BIT particles in an aqueous medium. After the milling is complete, the particle size of the resulting dispersion is measured by using a Hegman fineness gage, according to ISO 1520 test method (published by the International Organization for Standardization, Geneva, Switzerland). Preferred particle size is 5 micrometer or larger; more preferred is 10 micrometer or larger. Independently, the preferred particle size is 200 micrometer or smaller; more preferred is 100 micrometer or smaller; more preferred is 50 micrometer or smaller.

Some compositions of the present invention contain one or more organic solvent. Preferred are compositions that contain little or no organic solvent. When one or more organic solvent is present, the preferred amount is, by weight based on the weight of the composition, 10% or less; more preferred is 3% or less; more preferred is 1% or less. Most preferred are compositions that contain no organic solvent.

The composition of the present invention may optionally contain additional ingredients other than those discussed herein above. Suitable optional ingredients include, for example, one or more anti-foam agents, one or more stabilizers, one or more formulation aids, and combinations thereof.

It is to be understood that for purposes of the present Examples that each operation disclosed herein is performed at 25° C. unless otherwise specified.

EXAMPLES

Centrifuge Test

To test the ability of a composition to resist separation into distinct layers, a centrifuge test was used. Compositions were spun for 15 minutes at 3100 rpm at 1650G, using a Heraeus™ Megafuge™ 16 by Thermo Scientific. After spinning, compositions were inspected visually. If separate layers were observed, the percentage of the composition residing in each layer was reported.

Viscosity Measurement

The viscosity was measured using a Sheen™ 480 paddle viscometer, according to the test method ASTM D562 (American Society for Testing and Materials, West Conshohocken, Pa., USA). Results are reported in Krebs units. Compositions were tested immediately after they were made and again one day later.

Mixing

In the following examples, compositions were mixed as follows. Tap water and clay (if any) was added to a container and exposed to a disperser at 770 rpm for several minutes (typically 10 min). The disperser speed was reduced to 200 rpm and the dispersant (if any) was added while the disperser continued at 200 rpm for a few minutes. The water-soluble biocide (if any) was added and the disperser speed was kept at 200 rpm for another few minutes. Further water-soluble biocide (if any) was added while the disperser continued at 200 rpm for some minutes. The disperser was raised to 480 rpm, BIT was added, and the disperser ran for several minutes (typically 5-10 min) Organic acid and buffer (if any) were added, to adjust the pH to the preferred range (typically 4.5 to 2.5), as the disperser continued to run for several minutes. While the disperser continued at 200 rpm, polysaccharide was added, and then the disperser was run for 30 minutes at 200 rpm.

In the following examples, the amounts shown are percent by weight based on the total weight of each formulation.

Ratings for the centrifuge test: Ratings were determined based on the percentage of the composition contained in the largest phase, as follows:

| rating | meaning | largest phase percentage |
|---|---|---|
| "ex" = | excellent | 100% |
| "gd" = | good | less than 100%, and greater than 96% |
| "fr" = | fair | 96% or less, and greater than 91% |
| "pr" = | poor | less than 91%, and greater than 85% |
| "bd" = | bad | less than 85% |

Abbreviations

B1=mixture of biocides, with weight ratio of Bronopol to Kathon™ 886F (from Dow Chemical Company) of 4.41 to 1.

B2a=2-methyl-4-isothiazolin-3-one, from Dow Chemical Company

B2b blend of 2-methyl-4-isothiazolin-3-one with 5-chloro-2-methyl-4-isothiazolin-3-one, with 3:1 weight ratio of CMI to MI, from Dow Chemical Company B2=mixture of biocides B2a and B2b Clay1=Veegum™ smectite clay from R.T. Vanderbilt Co., Inc.

X1=Xanthan gum, from Danisco Grinsted

HEC=hydroxyethyl cellulose, from Dow Chemical Company.

P1=Byk P-105, dispersant, from Byk Chemie GmbH Company.

D1=Darvan™ No. 1, dispersant, from R.T. Vanderbilt Company.

M1=Metolat™ 388 dispersant, from Miinzing Chemie GmbH Company.

I1=Imbentin™ U/070 dispersant, from Kolb Distribution Ltd.

A33=Aculyn™ 33 thickener, Acrylic latex thickener, from Dow Chemical Company.

Visc-0=viscosity measured directly after preparation

Visc-1=viscosity measured after 1 day

TABLE 1

Examples 1-11:

| Example No.: | 1 | 2 | 3 | 4 | 5 | 6 | 7 | 8 | 9 | 10 | 11 |
|---|---|---|---|---|---|---|---|---|---|---|---|
| Ingredients | | | | | | | | | | | |
| BIT % | 20 | 20 | 20 | 20 | 20 | 20 | 20 | 20 | 20 | 20 | 20 |
| Other Biocide | | | | | | | | | | | |
| Other biocide % | | | | | | | | | | | |
| Polysaccharide | X1 | X1 | X1 | X1 | X1 | X1 | X1 | X1 | X1 | X1 | X1 |
| Polysaccharide % | 0.7 | 0.7 | 0.55 | 0.55 | 0.55 | 0.55 | 0.55 | 0.55 | 0.45 | 0.65 | 0.65 |
| Clay1 % | | | | 0.8 | | 0.8 | | | 0.8 | | |
| A33 % | | | | | | | | | | | |
| Dispersant | P1 | D1 | P1 | | P1 | P1 | M1 | | | | |
| Dispersant % | 0.3 | 0.3 | 0.1 | | 0.1 | 0.1 | 0.5 | | | | |
| Test Results: | | | | | | | | | | | |
| PS (micrometer) | 30 | 25 | 25 | 25 | 30 | 25 | 30 | 25 | 25 | 25 | 50 |
| Visc-0 (KU) | 89 | 67 | 75 | 77 | 75 | 75 | 66 | 68 | 69 | 69 | |
| Visc-1 (KU) | 87 | 66 | 73 | 76 | 75 | 75 | 66 | 66 | 65 | | 64 |
| Centrifuge | ex | gd | gd | ex | gd | gd | pr | gd | fr | gd | bd |

Ex 11 was prepared by mixing the ingredients without milling the mixture.

TABLE 2

Examples 12-16.3C (including comparatives 13C and 16.3C)

| Example No.: | 12 | 13C | 14 | 15 | 16.1 | 16.2 | 16.3C |
|---|---|---|---|---|---|---|---|
| Ingredient | | | | | | | |
| BIT % | 20 | 20 | 10 | 10 | 13 | 13 | 13 |
| Other Biocide | | | B1 | B1 | B2 | B2 | B2 |
| Other biocide % | | | 18.4 | 18.4 | %[1] | %[1] | %[1] |
| Polysaccharide | X1 | X1 | X1 | X1 | X1 | X1 | X1 |
| Polysaccharide % | 0.65 | 0.65 | 0.6 | 0.7 | 0.7 | 0.6 | 0.6 |
| Clay1 % | | | 1.4 | 1.4 | 1.0 | 1.0 | 1.0 |
| A33 % | | 4 | | | | | |
| Dispersant | | | | | | I1 | I1 |
| Dispersant % | | | | | | 0.2 | 0.4 |
| citric acid % | | | | | 0.4 | 0.3 | |
| sodium citrate % | | | | | 0.15 | | |
| Test Results: | | | | | | | |
| PS (micro-meter) | 25 | 15 | 25 | 25 | 25 | 25 | 25 |
| Visc-0 (KU) | 76 | 65 | 69 | 74 | 69 | 65 | 67 |
| Visc-1 (KU) | | | 70 | 75 | | | 68 |
| Centrifuge | ex | bd | gd | gd | gd | gd | ex |

Note
[1] the amount of other biocide was between 5 and 10 percent

TABLE 3

Examples 17C-22 (including comparatives 17C, 18C, and 19C)

| Example No.: | 17C | 18C | 19C | 20 | 21 | 22 |
|---|---|---|---|---|---|---|
| Ingredient | | | | | | |
| BIT % | 20 | 20 | 20 | 20 | 20 | 20 |
| Other Biocide | | | | | | |
| Other biocide % | | | | | | |
| Polysaccharide | X1 | X1 | X1 | HEC | HEC | HEC |
| Polysaccharide % | 0.3 | 0.4 | 0.5 | 0.6 | 0.8 | 1.0 |
| Clay1 % | | | | | | |
| A33 % | | | | | | |
| Dispersant | D1 | D1 | D1 | | | |
| Dispersant % | 2.0 | 2.0 | 2.0 | | | |
| Test Results: | | | | | | |
| PS (micro-meter) | 25 | 25 | 25 | 25 | 25 | 25 |
| Visc-0 (KU) | 51 | 54 | 60 | 65 | 89 | 107 |
| Visc-1 (KU) | 51 | 54 | 59 | | | |
| Centrifuge | bd | bd | bd | bd | gd | gd |

Comparative examples (marked with "C") all have bad results in the Centrifuge test (except for 16.3C, which had a higher level of dispersant than desired). The Examples of the invention generally had much better results in the Centrifuge test. Formulations without surface active agent or clay required at least 0.55% xanthan for good physical stability and at least 0.65% xanthan for excellent physical stability.

The same holds for formulations with low levels of suitable surface active substances (<0.3%) among which are e.g. P1 and D1. Formulations with xanthan (0.55%-0.7%) combined with clay (0.8%-1.4%) showed also good to excellent physical stability. Poor results were observed with M1. With HEC as sole thickener, about 0.8% was needed for good physical stability. HEC at 1% gave viscosity that was acceptable but higher than desired.

We claim:

1. A composition comprising 1,2-benzisothiazolin-3-one dispersed in an aqueous medium and further comprising one or more polysaccharide; wherein said polysaccharide is dissolved in said aqueous medium; and wherein
    said composition comprises no surface-active compound,
        further wherein wherein the amount of said polysaccharide is 0.5% to 1.5 by weight, based on the weight of said composition;
    and further wherein the amount of said 1,2-benzisothiazolin-3-one is 10% to 40% by weight, based on the weight of said composition.

2. The composition of claim 1, wherein said polysaccharide comprises xanthan gum, hydroxyethyl cellulose, or a mixture thereof.

3. The composition of claim 1, wherein said composition additionally comprises one or more biocide that is not 1,2-benzisothiazolin-3-one.

* * * * *